(12) United States Patent
Vitaletti (10) Patent No.: US 9,400,868 B2
(45) Date of Patent: *Jul. 26, 2016

(54) METHOD COMPUTER PROGRAM AND SYSTEM TO ANALYZE MASS SPECTRA

(71) Applicant: International Business Machines Corporation, Armonk, NY (US)

(72) Inventor: Marcello Vitaletti, Rome (IT)

(73) Assignee: International Business Machines Corporation, Armonk, NY (US)

( * ) Notice: Subject to any disclaimer, the term of this patent is extended or adjusted under 35 U.S.C. 154(b) by 99 days.

This patent is subject to a terminal disclaimer.

(21) Appl. No.: 14/054,893

(22) Filed: Oct. 16, 2013

(65) Prior Publication Data

US 2014/0052385 A1 Feb. 20, 2014

Related U.S. Application Data

(63) Continuation of application No. 13/698,376, filed as application No. PCT/EP2011/057835 on May 16, 2011.

(30) Foreign Application Priority Data

Jun. 10, 2010 (EP) .................................... 10165533

(51) Int. Cl.
*G01N 1/02* (2006.01)
*G01N 1/00* (2006.01)
(Continued)

(52) U.S. Cl.
CPC .............. *G06F 19/00* (2013.01); *G06F 19/703* (2013.01); *G06K 9/00496* (2013.01); *H01J 49/0036* (2013.01)

(58) Field of Classification Search
CPC ................................................... G06K 11/00

USPC ................... 702/19, 20, 23, 27, 56, 187, 188; 324/307, 309; 356/456; 506/9
See application file for complete search history.

(56) References Cited

U.S. PATENT DOCUMENTS 5,072,115 A 12/1991 Zhou
5,440,388 A * 8/1995 Erickson ....................... 356/456
(Continued)

FOREIGN PATENT DOCUMENTS

JP S62124456 A 6/1987
JP 2004317509 A 11/2004
(Continued)

OTHER PUBLICATIONS

Brigitte Chiarizia, PCT Notification of Transmittal of the International Search Report and the Written Opinion of the International Searching Authority, or the Declaration, International Application No. PCT/EP2011/057835, Date of Mailing Jan. 26, 2012, 12 pages.
K. Magnus Aberg et al., The correspondence problem for metabonomics datasets, Analytical and Bioanalytical Chemistry, Springer, Berlin, DE, vol. 394, No. 1, Feb. 7, 2009, pp. 151-162.
(Continued)

*Primary Examiner* — Gregory J Toatley
*Assistant Examiner* — Felix Suarez
(74) *Attorney, Agent, or Firm* — Jay Wahlquist; Daniel R. Simek (57) ABSTRACT

A method, computer program and system to identify peaks generated by different physical ions in a solution including substances by analyzing mass and intensity coordinates of all peaks in a set of mass spectra measured with errors for a certain concentration c of the solution is here disclosed. The peaks in different mass spectra are associated to a same ion if they are sufficiently 'close' according to specific discrimination criteria that go beyond the proximity of mass values.

15 Claims, 6 Drawing Sheets

(51) Int. Cl.
  *G01N 1/22* (2006.01)
  *G01N 1/28* (2006.01)
  *G06F 19/00* (2011.01)
  *G06K 9/00* (2006.01)
  *H01J 49/00* (2006.01)

(56) References Cited

U.S. PATENT DOCUMENTS

| | | | |
|---|---|---|---|
| 7,361,889 B2 | 4/2008 | Yamaguchi | |
| 8,188,011 B1 * | 5/2012 | Griffey et al. | 506/9 |
| 2002/0138210 A1 * | 9/2002 | Wilkes et al. | 702/28 |
| 2002/0145425 A1 * | 10/2002 | Ebbels et al. | 324/309 |
| 2003/0036207 A1 | 2/2003 | Washburn et al. | |
| 2004/0195500 A1 | 10/2004 | Sachs et al. | |
| 2005/0063864 A1 | 3/2005 | Sano et al. | |
| 2005/0065732 A1 * | 3/2005 | Tilton et al. | 702/19 |
| 2005/0255606 A1 | 11/2005 | Ahmed et al. | |
| 2013/0073219 A1 | 3/2013 | Vitaletti | |

FOREIGN PATENT DOCUMENTS

| | | |
|---|---|---|
| JP | 2007525645 A | 9/2007 |
| WO | 2009/103050 A1 | 8/2009 |

OTHER PUBLICATIONS

Katharina Podwojski et al., Retention time alignment algorithms for LC/MS data must consider non-linear shifts, Bioinformatics, vol. 25, No. 6, Jan. 28, 2009, pp. 758-764.

Tianwei Yu et al., apLCMS-adaptive processing of high-resolution LC/MS data, Bioinformatics, vol. 25, No. 15, May 4, 2009, pp. 1930-1936.

Francesca Forner et al., Mass Spectrometry Data Analysis in the Proteomics Era, Current Bioinformatics, vol. 2, No. 1, Jan. 1, 2007, pp. 63-93.

Clemens Gropl et al., Algorithms for the Automated Absolute Quantification of Diagnostic Markers in Complex Proteomics Samples, Computational Life Sciences Lecture Notes in Computer Science, Lecture Notes in Bioinformatics, Springer, Berlin, DE, Jan. 1, 2005, pp. 151-162.

Ole Schulz-Trieglaff, Computational Methods for Quantitative Peptide Mass Spectrometry, Berlin, Oct. 1, 2008, 42 pages.

European Patent Application No. 11719824.2-1901, Office Action Communication, FR920100003, Apr. 25, 2014, 4 pages.

Chinese Application No. 201180025378.1, Office Action Communication, Oct. 27, 2014, 6 pages.

* cited by examiner

METHOD COMPUTER PROGRAM AND SYSTEM TO ANALYZE MASS SPECTRA

REFERENCE TO PRIOR APPLICATIONS

The current application is a continuation application of U.S. Utility application Ser. No. 13/698,376, which was filed on 16 Nov. 2012, which is hereby incorporated by reference, and which claimed the benefit of European Patent Application No. EP10165533.0, which was filed on 10 Jun. 2010.

FIELD OF INVENTION

This invention generally relates to mass spectra analysis; more particularly the invention provides a method for analyzing mass spectra of chemical solutions.

BACKGROUND ART

The mass spectrometry principle consists in ionizing chemical elements to generate charged molecules or molecule fragments for which the mass-to-charge ratio will be measured. Mass spectra of ions, for example in a solution, provide a distribution of the ions by mass-to-charge ratio. The x-axis of a mass spectrum graph gives the mass-to-charge ratio identifying one ion and the y-axis gives the signal intensity provided by these ions. A mass spectrum graph for one ion gives the (mass-to-charge, intensity) information for the ion read at the peak. For a chemical solution containing different ions, each peak of the mass spectrum graph may indicate the presence of a corresponding ion in the solution.

However it is not always easy to identify ions in a mass spectrum of a chemical solution when the mass spectrum graph contains a dense sequence of peaks and when—for each peak—both the mass and the intensity measured by the instrument are subject to errors. For instance, we may need to predict concentration of a soluble substance in a solution by building regression models, the concentration of some ions in the solution being an unknown yet definite function of the substance concentration. In the linear case the ions concentrations are related to the substance concentration by coefficients which are different for different ions. In order to build the regression models we must first be able to identify the peak intensity corresponding to a same ion in different mass spectra for different concentrations of a substance in a solution. When the substance corresponds to inorganic molecules the ions are easily identified in the mass spectra. However, in the case where an organic molecule is diluted in water the mass spectrum of the resulting solution may include hundreds of ions, due to the dissociation of the large molecule in water.

One prior art solution to identify in different mass spectra corresponding to different concentration of a substance in a solution, the information corresponding to a same ion, is to use a well known data binning technique. The data binning technique allows to reduce the effect of minor measurement errors: in the mass spectrum the mass range should be covered by non-overlapping intervals (bins) of uniform size (usually of one mass unit) and the intensity of each peak is accumulated into the corresponding bin. However, let $m_e$ be the error associated to the ion mass measurement across all solutions to be analyzed for building the regression model, two effects related to the error $m_e$ may undermine the binning approach, namely:

With a bin size comparable to (or smaller than) $m_e$ it is likely that the peak of a given ion in different spectra would be accumulated in different bins;

With a bin size larger than $m_e$ it generally happens that the peaks of two or more ions with similar masses are accumulated in the same bin. However those ions may have a totally different linear dependency on the substance concentration and, because of the previous effect, the same bin may accumulate the contributions from different ions across different spectra.

There is thus a need to have a method for identification of in mass spectra graph peaks corresponding to the same physical ion across solutions prepared with different known concentrations of a substance.

SUMMARY OF THE INVENTION

It is an object of the present invention to define a method for identifying peaks corresponding to the same ion in different mass spectra in a reliable way.

The object is reached with a method performed on a computer to identify peaks generated by different physical ions in a solution including a certain concentration of at least one substance by analyzing mass and intensity coordinates of all peaks, measured with errors, coming from a set of mass spectra data files, the method comprising, reading coordinates of a peak from a first mass spectrum data file in the set of mass spectra data files;

selecting from each the mass spectrum data file other than the first mass spectrum data file, peak coordinates which are close to the read peak coordinates from the first mass spectrum, by computing a distance function qualifying a proximity between two peaks;

determining the highest scored sequence of peaks comprising the read peak from the first mass spectrum and one selected peak from each other mass spectrum by computing a score function qualifying the likelihood that all peaks in the sequence have been generated by the same type of physical ion;

storing the highest scored sequence only if the ratio highest scored/second highest scored sequence is above a limit ratio;

reading coordinates of one other peak from the first mass spectrum data file and executing the preceding selecting, determining and storing steps until all the peaks from the mass spectrum are read, each of the resulting sequences containing peaks, one for each mass spectrum, identified as being generated by a same physical ion.

The object is also reached with a method further comprising:

suppressing among the stored sequences any subset of sequences which are found to include a same peak of a same mass spectrum.

The object is also reached with a method further comprising wherein the distance function between two peaks and the scoring function depend on the mass and intensity of the two peaks.

The object is also reached with a method further comprising wherein the distance function between two peaks depends on the mass of the peaks and the scoring function depends on a combination of the mass of the peaks and the peak concentration-intensity correlation.

The object is also reached with a method further comprising wherein the identifying the resulting peak sequences corresponding to ions is executed on a first set of mass spectra for a given c concentration using a first distance and a first scoring function which both depend on the mass and intensity of the peaks; the method further comprising:

repeating the preceding steps on further sets of mass spectra, the first and further sets of mass spectra corresponding to different concentrations;

computing average mass-intensity peak coordinates for each sequence resulting from execution of the preceding steps for each solution concentration and obtaining a series of virtual peaks per each concentration;

applying the steps of the method to the set of virtual mass spectra, each virtual mass spectrum corresponding to one concentration, each virtual mass spectrum comprising the computed series of virtual peaks, using a second distance function between two peaks which depends on a combination of the mass of the peaks and the peak concentration-intensity correlation, the resulting sequences being the peaks corresponding to an ion in the different 'virtual mass spectra', each 'virtual mass spectrum' corresponding to one solution concentration.

The object is also reached with a method further comprising wherein the first distance d function between two mass spectra peaks $P_1$ with coordinates $x_1$ and $y_1$ and $p_2$ with coordinates $x_2$ and $y_2$ is:

$$d(p_1,p_2) = \sqrt{(x_1-x_2)^2 + (y_1-y_2)^2/R^2}$$

R being the ratio between the relative errors associated to the y coordinate and x coordinate.

The object is also reached with a method further comprising wherein the first scoring of a sequence is:

$$1/\max d(p1,p2)$$

where p1, p2 are any two peaks in the sequence and d (p1, p2) is the distance between them.

The object is also reached with a method further comprising wherein the second distance d function between two mass spectra peaks $P_1$ and $p_2$ with coordinates $x_1$ and $y_1$ and $p_2$ with coordinates $x_2$ and $y_2$ is:

$$d(p_1,p_2) = \text{absolute value}(x_1-x_2).$$

The object is also reached with a method further comprising wherein the second scoring of a sequence is:

$$\text{correlation\_coefficient}(c1,y1,c2,y2,\ldots cN,yN)/\max d(p1,p2)$$

where p1, p2 are any two peaks in the sequence and d (p1, p2) is the distance between them.

The object is also reached with a system comprising means adapted to carry out the steps of the method.

The object is also reached with a computer program comprising instructions for carrying out the steps of the method when the computer program is executed on a computer.

Some advantages are obtained by applying the first stage of the proposed two-stage filtering process to data obtained from a mass spectrometer.

One advantage is that the method provides an indication of the amount of errors associated with a measurement of the mass value and of the error associated to the measurement of the intensity value for all those peaks which are retained in the filtered spectra.

Another advantage is that a large amount of discarded peaks would provide an early indication of quality problems in the measurement namely of problems associated to a non perfect standardization of the measurement conditions (for example because of samples being measured at different temperatures or far from a steady state of equilibrium) or because of the uncontrolled presence of contaminants in some of the samples.

A further advantage is that peaks generated by ions with very similar or identical mass but different structure would be eliminated from the filtered spectra, thus simplifying the work of building a model relating the composition of a given solution to a measured spectrum.

According to a second aspect of the present invention, there are advantages obtainable by applying the second stage of the proposed two-stage filtering process to data which have passed the first stage.

One advantage is that peaks generated by ions whose concentration in the solution is far from a linear function of the concentration of the substance of which samples are measured at different concentrations are eliminated from the filtered spectra. This simplifies the work of building a linear model relating the composition of a given solution to a measured spectrum.

Another advantage is that a large amount of discarded peaks would provide an early indication of quality problems in the data (for example because of samples being measured at different temperatures or far from a steady state of equilibrium) or they could indicate a complex (non-linear) relationship between the concentration of an "identified ion" and the concentration of the substance of which samples are measured at different concentrations. In the first case, better data could be obtained by a more controlled process and the risks of exploiting inaccurate data is avoided. In the second case, it may be necessary to construct a non-linear model of the data and the risks of false assumptions in the exploitation of the data can be avoided.

DETAILED DESCRIPTION OF THE INVENTION

Figure 1:
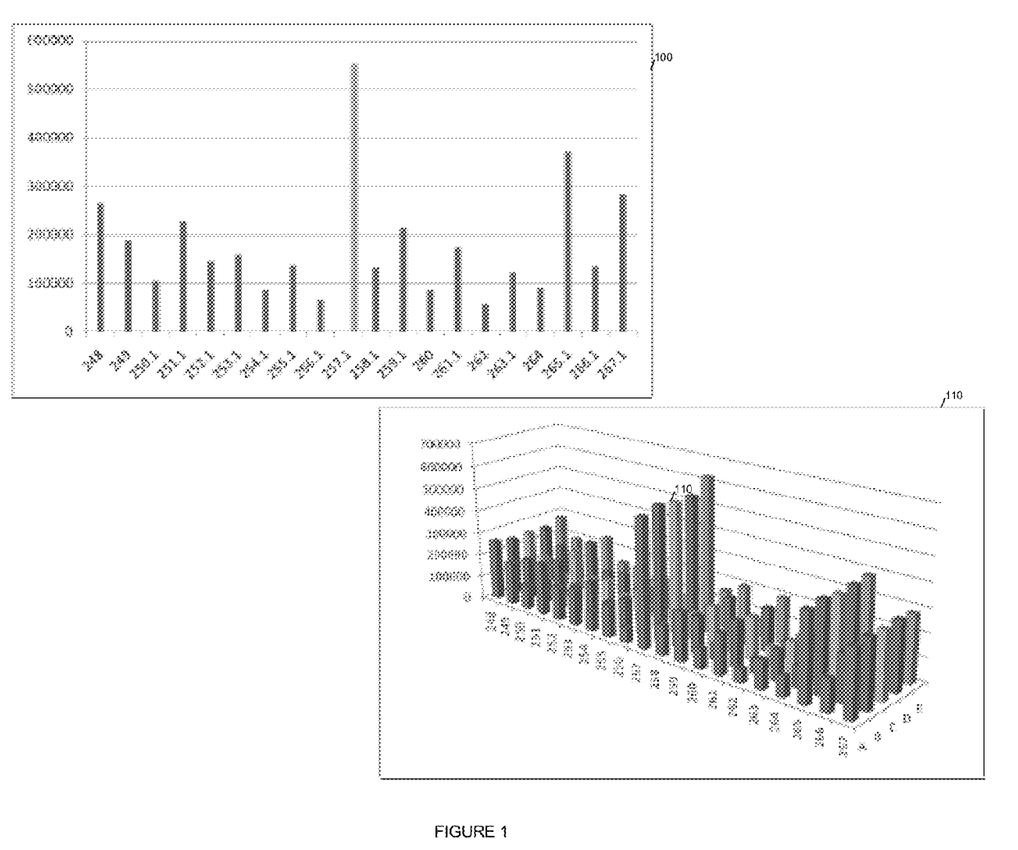
FIG. 1 shows details of a first mass spectrum measured on one sample of a chemical solution and a visualization of five mass spectra (A, B, C, D, E) obtained on different samples from the same solution.

FIG. 1 shows details of a first mass spectrum measured on one sample of a chemical solution and a visualization of five mass spectra (A, B, C, D, E) obtained on different samples from the same solution. The first chart (100) is partial view of a mass spectrum of ions in a water solution containing 5 parts per million of a chemical substance around a peak of mass 257.1 and intensity above 500000 in the units used for the mass spectrometer output. The entire spectrum contains about 1500 peaks. The second mass spectrum (110) is obtained by repeating the measurement on the same sample with the same instrument, the values associated to the same peak oscillate by 0.1% in the mass value and about 10% in the intensity value. In the second 3D diagram (110) the mass errors were artificially forced to be constantly zero. In this case peaks (115) can be easily identified as representing the same ion. The problem is how to identify the peaks in different samples corresponding to a same ion if both the mass (x value) and the intensity (Y value) are subject to measurement errors. When the error affecting the mass measurements of two ions exceeds the difference between their "true" masses, it is impossible to identify that two peaks in different spectra belong to the same ion. Even if the error is relatively small, implementing a robust "identification" process in a computer program requires specific discrimination criteria going beyond the proximity of mass values.

Figure 2:
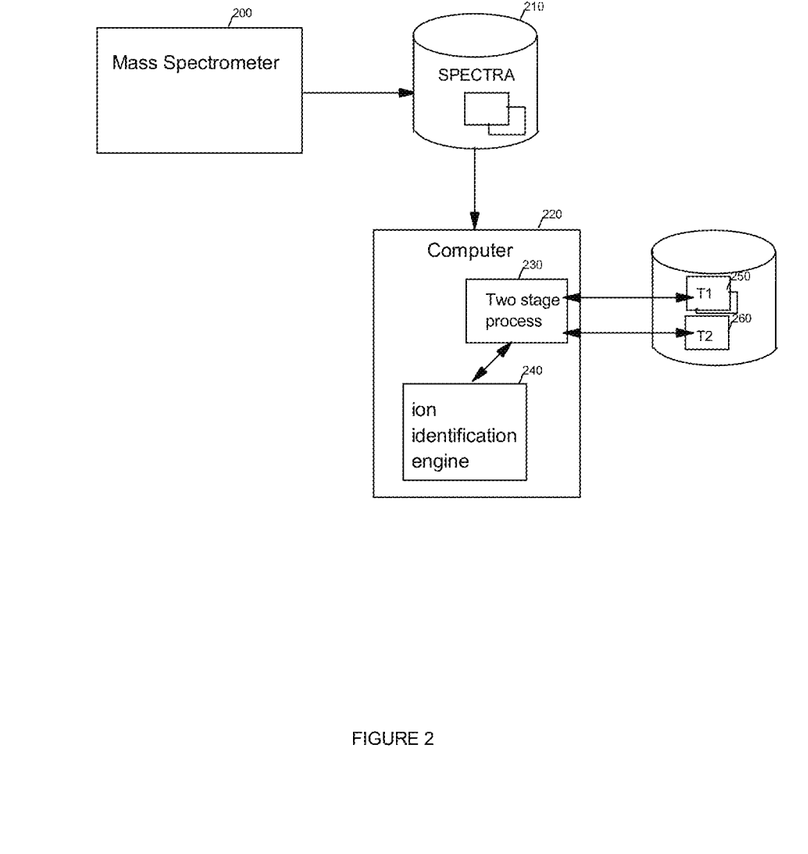
FIG. 2 illustrates the environment wherein the method of an embodiment is implemented.

FIG. 2 illustrates the environment wherein the method of an embodiment is implemented. FIG. 2 shows the context of the invention. Solutions with varying known concentrations of a given chemical substance are analyzed by a mass spectrometer (200) producing data files (spectra 210). A spectrum contains a sequence of peaks, a peak being described by its mass-to-charge ratio and signal intensity values (the peak coordinates in a graphic representation) measured by the spectrometer.

It is noted also that if the method is applied to a solution containing only one substance, this method will help to determine the peak values of the solution at different concentration of the substance, this will help in determining a linear model helping to determine the presence of a substance in a solution at a specific concentration.

The mass spectrum data files are processed in an embodiment by programs operating on a computer (220). Still in an embodiment, the ion identification method comprises an identification process engine (240) which is applied in a two stage process program (230). The ion identification engine applies in each stage different discrimination criteria. In the first stage the ion identification engine applies a mass-intensity based proximity criterion as described later on in the document in relation with the description of FIG. 4. The first stage takes as input mass spectra files (210) produced by the spectrometer and produces ion tables (T1), one row representing peaks in different spectrum corresponding to one ion. The mass spectra processed in stage 1 are those corresponding to a set of measurement samples done on a solution containing a certain concentration of a chemical substance, the output applied to one sample set being one ion table (T1). The operation is repeated for N sets of mass spectra corresponding to N different concentrations of the chemical substance. The output of stage 1 results in N ion tables (T1 250), one per set of samples, each one corresponding to a concentration of the solution.

In the second stage the ion identification engine is executed once. For peak identification it applies a discrimination criterion which is a combined mass-proximity and concentration-intensity correlation criterion as described later on in the document in relation with the description of FIG. 4 The second stage uses as input the ion tables created during stage 1 which are converted into 'virtual mass spectra' and gives as output one identified ion table (T2 260). The output ion table, T2, provides for each ion identified in the solutions, in each row, a reference to a series of peaks coordinates for each concentration.

In an embodiment, the invention is implemented as a computer program product accessible from a computer-usable or computer-readable medium providing program code for use by or in connection with a computer or any instruction execution system. It is noted that the invention can take the form of an entirely hardware embodiment, an entirely software embodiment or an embodiment containing both hardware and software elements. In an embodiment, the invention is implemented in software, which includes but is not limited to firmware, resident software, microcode, etc.

Figure 3:
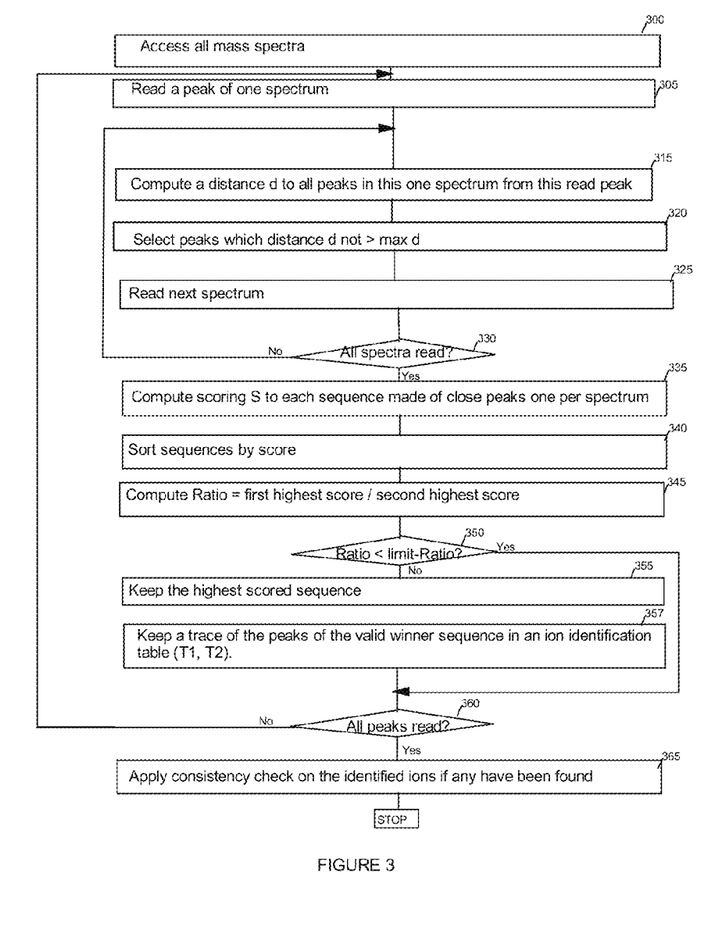
FIG. 3 is the flowchart of the ion identification method which can be used with different identification criteria according to an embodiment.

FIG. 3 is the flowchart of the ion identification method which can be used with different identification criteria according to an embodiment. The flowchart describes the ion identification method allowing to identify peaks corresponding to the same ion type as they occur in different spectra obtained from solutions in which one substance is present in different concentrations.

To illustrate the ion identification method we use mass spectra as inputs. This simplifies the comprehension of the steps of the method even if, as stated in description of FIG. 2, in stage 2 the inputs are not directly mass spectra but the ion identification tables T1 which are converted into 'virtual mass spectra'. As a matter of fact, the output T1 tables refer in each row to peaks corresponding to a same ion in the different mass spectra which have been used as input: an average of peak coordinates are computed for each row of each T1 table to obtain the 'virtual mass spectra'.

In a first step (300) the mass spectra are all accessed. As already said the mass spectra provides peaks with their X coordinate being the mass-to-charge ratio (called mass in the rest of the document) and Y coordinate being the intensity of the signal (called intensity in the rest of the document). All the mass spectra correspond to measurement samples of a same solution having a certain concentration of a chemical substance soluble in a solution, this substance needed to be analyzed. The M spectra are numbered from 1 to M.

The mass spectra access means that the mass spectrum data files containing coordinates of peaks are read by the computer and preferably stored in memory as a data structure. One example of such data structure used by the ion identification engine is described later on the document in relation with description of FIG. 5. One table is built per mass spectrum. Each table row may store the coordinates of a peak of the mass spectrum.

In step 305 one peak is read on one of the M spectra. The one spectrum in which one peak is read contains N1 peaks indexed from 1 to N1 and an iteration over all those peaks is initialized (see test 360 later on in the flowchart). The read peak is taken as the basis for the successive identification of corresponding peaks from the remaining spectra. According to the following process the peak representing a potential ion in this first spectrum is analyzed. The inner iteration over the remaining spectra is initialized (see test 330 later on in the flowchart).

An appropriate "distance" function between two peaks is used to find a certain number of peaks in the current spectrum which are the closest to the one currently selected in step 305. At least one peak and a limited number of peaks are selected by limiting the distance to a pre-defined distance max d,(320). It is possible, if limiting the search within the pre-defined distance that no peaks are found. It is noted that the choice of the 'distance' function is based on criterion a mass-intensity based proximity in stage 1 and a mass-proximity criterion in stage 2. The distance functions are more detailed later on in the document in relation with the description of FIG. 4.

By reading all the spectra (executing the loop on answer no to test 330) all possible candidate sequences of M selected peaks are created using the current peak from the first spectrum and candidate peaks found in the spectra from 2 to M. The total number of such sequences is equal to the product $n_2 \times n_3 \times \ldots \times n_M$ where $n_i$ is the number of candidate peaks found on the spectrum with index "i" and M is the number of peaks in each sequence. In step 335 an appropriate scoring function is applied to each sequence to compute a scoring value. The function must be chosen so that high scoring values should only be obtained for sequences where the peaks are all expression of the same type of ion. The choice of the scoring function depends on ion identification criteria chosen; the scoring function will be more detailed later on in the document in relation with the description of FIG. 4.

In the next step (340) the sequences created in the preceding steps are sorted by the corresponding score values computed in step 335, the highest score corresponding to the first position in the sorted list of sequences.

In the next step (345) a "Ratio" variable is computed as the ratio between the first score and the second score in each sequence. The scoring function used in step 335 produces a value of the Ratio variable significantly above unity to indicate that a single sequence winner has emerged from the contest. The computed value of Ratio is compared in step 350 against a pre-defined threshold (limit-Ratio). A value below the threshold indicates no clear sequence winner meaning that no identification is possible for the current ion. The sequence with the highest score value and for which the Ratio variable equals or exceeds the limit-Ratio is kept for this peak read in step 305.

A trace is kept (357) of the (X mass,Y intensity) values of each sequence member of the valid winner sequence (if there is any), each member of the sequence being one peak in each spectrum, all peaks corresponding to the same ion. This information may be kept in an ion identification table (T1, T2) as described in relation with the description of FIG. 5 or 6 later on in the document.

The following step (360) is performed also if there is no valid winner sequence for a peak read and ion identification candidate (answer no to test 350). If all peaks are not read in the one spectrum (answer No to test 360) the same loop from step 315 to 360 is executed to identify the highest scored sequence identifying an ion in each spectrum.

When all peaks have been read for the one spectrum used for this algorithm (answer Yes to test 360) all peaks in the one spectrum for which a winner sequence has been produced can be tentatively considered to have been generated from the same physical ion. A global consistency check (365) is performed by examining the resulting sequences of peaks. A resulting sequence of peaks in each sequence is the expression of a specific ion type only if each peak appears once in each sequence. Sequences that have one or more peaks in common are thus discarded. The remaining sequences can be used with a higher level of confidence with respect to the original data. In fact, each sequence characterizes the response of the instrument to the presence of a specific (although unknown) ion type. At the end of the execution of the flowchart, the final ion identification table contains only the references to the sequences of peaks confirmed by the global consistency check. However the global consistency step is optional because all the sequences selected by the preceding steps may lead to a correct result.

Figure 4:
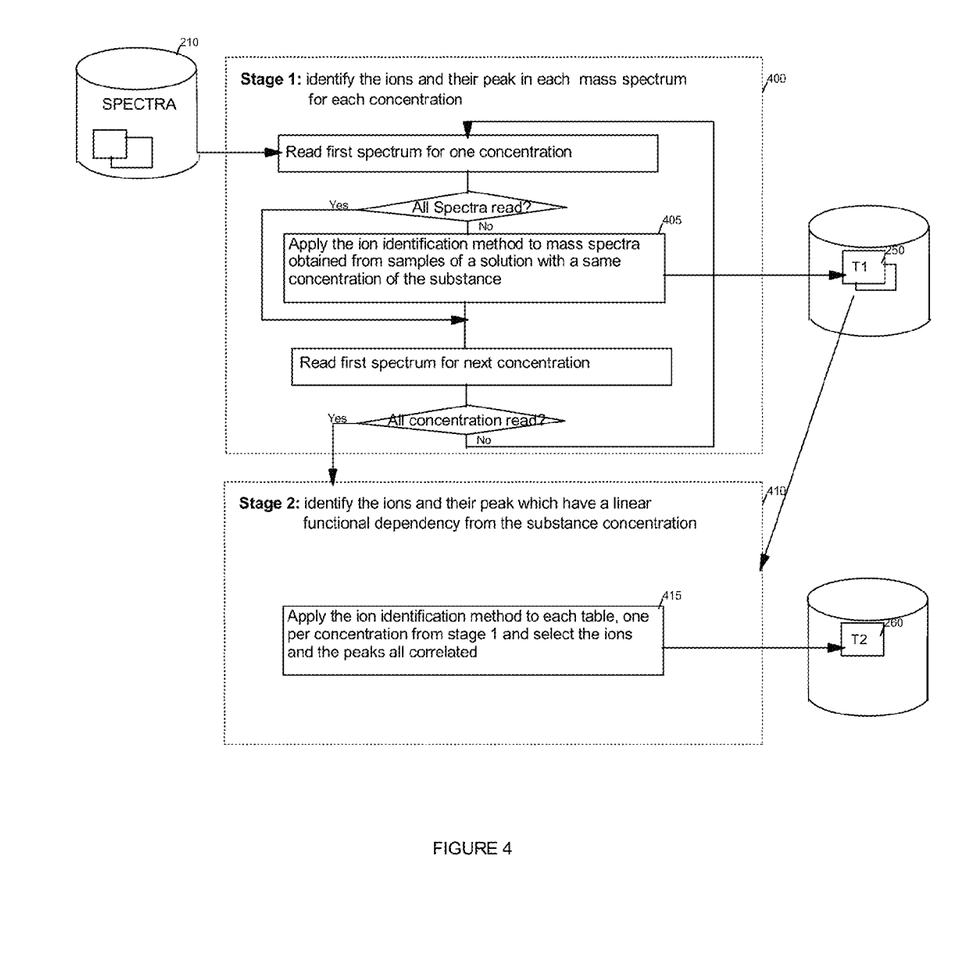
FIG. 4 is the general flowchart of the method to identify the same ion in mass spectra corresponding to different known concentrations of a substance applying the method of FIG. 3 according to an embodiment.

FIG. 4 is the general flowchart of the method to identify the same ion in mass spectra corresponding to different known concentrations of a substance applying the method of FIG. 3 according to an embodiment. In this flowchart two complementary implementations of the ion identification process of FIG. 3 are connected in a two-stage pipeline. The first stage of the pipeline uses as input series sets of spectra produced by the spectrometer measuring solutions with different concentrations. The second stage of the pipeline takes in input the data output by the first stage and produces the final output which is for each ion a reference to peak coordinates for each concentration.

In stage 1 (400) the ion identification process is applied to multiple spectra obtained from solutions which contain the same substance at (N) different levels of the concentration. Multiple (M) spectra are obtained by the instrument for each level of the concentration, either by repeating the measure M times on the same sample or by taking the measure from M equivalent samples. This means that the method as described with the flowchart of FIG. 3 is processed (405) on each set of samples mass spectra measured for one solution concentration. A mass-intensity based proximity criterion is used for identifying ions across spectra of solutions with the same (known or unknown) concentration of one or more substances. With this method, M peaks from corresponding spectra are said to be "generated by the same ion" if they are "the closest to each other" based on a proper distance function which depends on the X and Y coordinates of two peaks and on the different sizes of the relative error affecting the measurements of mass (the x's) and, respectively, of the ions concentration (the y's). The output from stage 1 includes a sequence of M peaks for each identified ion and for each level of the concentration. T1 Ion identification tables being one example of way to keep the information resulting of the ion identification method of FIG. 3 are described later on in the document in relation with the description of FIG. 5.

The distance function and the scoring function used respectively in step 315 and step 335 of the identification process performed in stage 1 are chosen according to a mass-intensity based proximity criterion. Any "distance" function $d(p_i, p_j)$ between two "points" (peaks) must be such that $d(p_i, p_j)$ vanishes for i=j while it is always positive otherwise. Associated with each peak are two coordinates (x and y) representing the ion mass (x) and the signal intensity (y) thus it is possible in principle to take for a distance function the standard Euclidean distance in two-dimensional space based on the x and y coordinates of two peaks. This however is not suitable without corrections as it does not account for the different scales and precision associated to the x and y coordinates of a point (peak). The examination of mass spectra from an ordinary instrument shows that the mass (x coordinate) value is determined with a relative error of about 0.1% while the intensity (y coordinate) is determined with a relative error of about 10% hence two orders of magnitude higher. Defining R as the ratio between the relative errors associated to the y coordinate and to the x coordinate, the proposed distance function is the following, x1, y1 being the coordinates of peak p1 and x2, y2 being the coordinates of peak p2:

$$d(p_1,p_2)=\sqrt{(x_1-x_2)^2+(y_1-y_2)^2/R^2}$$

The calculation of a scoring value in step 335 of the ion identification process is performed on each "candidate sequence" of peaks. The scoring function is thus a function of the set of peaks in the candidate sequence. In stage 1 this function is simply the reciprocal of the distance function (the one employed in block 315) for the two peaks in the sequence that are farthest apart from each other. The scoring function is: 1/max d(p1, p2) where p1 and p2 are any two peaks in the sequence.

Therefore, the "closest to each other" are peaks in a sequence, the higher is the scoring value assigned to the sequence. The combination of the above distance function and scoring function are found adequate for the ion identification process performed in stage 1 where all spectra are taken from samples with the same concentration of a given substance.

The process of the flowchart of FIG. 4 continues with stage 2 (410) for which the inputs are the ion identification tables (such as T1) created in stage 1.

The data contained in the ion identification tables are equivalent to mass spectra data as already mentioned. Each sequence of peaks corresponding to an ion "identified" in stage 1 is effectively replaced with a "virtual" peak whose mass and intensity are obtained by averaging over the sequence. In stage 2 the process of the ion identification method as described with the illustrative flowchart of FIG. 3 is applied (415) to these virtual peaks. The objective is to "identify" virtual peaks generated by the same ion across spectra measured from samples with a different level of the substance concentration. A combined mass-proximity and concentration-intensity correlation criterion is used for identifying ions across spectra of solutions at L different known concentrations of one given substance. With this method, a sequence of L peaks is said to "belong to the same ion" if it maximizes an "optimality measure" which weights the product of "closeness" with respect to the mass and the "strength of linear correlation" between the values of concentration C and of intensity Y across the peaks. The distance and scoring functions are defined taking into account the ion identification criterion for stage 2. The use of these distance and scoring functions is to filter out sequences of peaks which do not show a strong linear correlation between the substance concentration and the intensity values. The output from stage 2 provides a sequence of "virtual peaks" for the same ion, each "virtual peak" corresponding to a different level of concentration. In this form, the information derived from the spectrometer can be exploited by applications—not part of the present invention—aimed at building a model of the mass spectrum where the intensity observed on a number of selected peaks (channels) is a linear function of the concentration of one or more substances. The T2 Ion identification table being one example of way to keep the information resulting of the ion identification method of FIG. 3 is described later on in the document in relation with the description of FIG. 6.

The distance function and the scoring function used respectively in step 315 and step 335 of the identification process performed in stage 2 are chosen according to the combined mass-proximity and concentration-intensity correlation criterion. In stage 2 one cannot expect peaks generated by the same ion to exhibit similar values for the intensity across spectra, because the latter are taken at different concentrations of the substance. For this reason, the distance function used in stage 2 depends only on the x coordinate (ion mass) of a peak:

$$d(p_1, p_2) = \mathrm{abs}(x_1 - x_2),$$

where abs( ) is the absolute value function.

The calculation of a scoring value in block 335 of the ion identification process is performed on each "candidate sequence" of peaks. The scoring function is thus a function of the set of peaks in the candidate sequence. In stage 2 it is possible in principle to take for a distance function the statistical correlation coefficient. The idea is that a high correlation coefficient (close to unity) would only result from peaks which correspond to the same physical ion (and exhibiting a response which is linear with the substance concentration). However, experiments conducted with real data showed that in this case the ratio between the scoring values (equal to correlation coefficient) on the highest scoring sequences would often be very close to unity, making it impossible to decide on a clear "winner". A more appropriate scoring function should also take into account the proximity of mass values for all peaks in a sequence. Therefore, the proposed scoring function is taken as the product of two terms. One term is the correlation coefficient calculated over peaks of a sequence, where substance concentration is the independent variable and peak intensity is the dependent variable. The second term is the reciprocal of the distance function (the one employed in block 315) for the two peaks in a sequence that are farthest apart from each other.

The scoring function is:

$$\mathrm{correlation\_coefficient}(c1, y1, c2, y2, \ldots cN, yN) / \max d (p1, p2)$$

where p1, p2 are any two peaks in a sequence and d (p1, p2) is the distance between them.

The combination of the above distance function and scoring function are found adequate for the ion identification process performed in stage 2 where spectra are taken from samples with different concentrations of a given substance.

Figure 5:
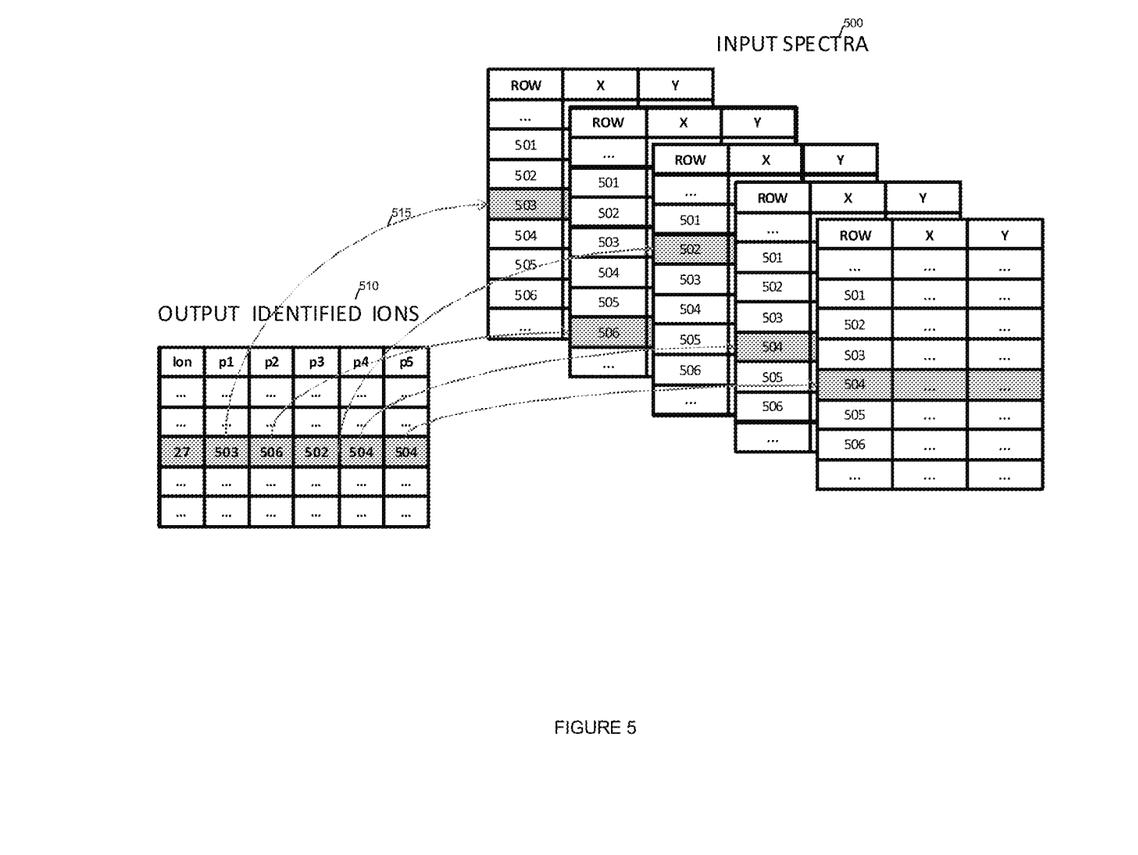
FIG. 5 shows the data structure of inputs to stage 1 of the general flowchart of FIG. 4 and the data structure of stage 1 output according to an embodiment.

FIG. 5 shows the data structure of inputs to stage 1 of the general flowchart of FIG. 3 and the data structure of stage 1 output according to an embodiment. Particularly the output table as the one described in FIG. 5 is one way to represent the result of stage 1 applying the ion identification method using a distance and scoring function according to a mass-intensity based proximity criterion.

The input (500) comes from—for a given concentration of a substance in the solution sample—M spectra, obtained by repeating the measurement M times or by applying the measurement to M identical samples. Each spectrum data read from data files by the computer can be stored in memory as a table with two columns (X and Y) where—on each row—the ion mass measure by in the X column and the corresponding measured intensity in the Y column.

The output (600) may be represented by a table (T1) of M columns—one for each measured spectrum—and as many rows as there were identified ions at the end of stage 1. Each row contains pointers (515) to the peaks which are assumed to have been generated by the same physical ion in each one of the M input spectra. Each row contains pointers corresponding to a same winner and valid sequence which obtained the highest score with an acceptable scoring ratio.

For example the row number 27 (27 is one row index value in the table) marked with a gray background in the output table contains the numbers 503, 506, 502, 504, 504, which give the positions in the input spectra of the identified ion. This means that the peak at row 503 of the first input spectrum,
the peak at row 506 of the second input spectrum,
etc.

have been "identified" by the stage 1 process, thus it can be safely assumed that those peaks have been generated by the same physical ion.

By taking the average and spread of the M values of mass (X) and intensity (Y) corresponding to a given row of the output table, one estimates the size of the errors affecting the measurement of those quantities.

The information associated to a given row in the above output table can be reduced by defining a "virtual peak" of which mass and intensity values are averages of the corresponding values over the M "identified" peaks. Alternatively, one can consider the minimum and maximum values of the mass and intensity for each row, thus defining a "virtual peak" by an interval $[x_{min}, x_{max}]$ for the mass and by an interval $[y_{min}, y_{max}]$ for the intensity.

A specific use of the ion identification method applied as described in FIG. 4 allows using the results to build a linear model relating the composition of a given solution to a measured spectrum. In this case, the stage 1 inputs are mass spectra measured for one solution including only one single substance at different known concentrations. In this way, the ion identification table (T1 510) contains the ions identified with their reference X,Y peak values in each mass spectrum for a given concentration.

Such an ion identification table (T1, 500) is built for each solution concentration for which a set of mass spectra has been obtained.

Figure 6:
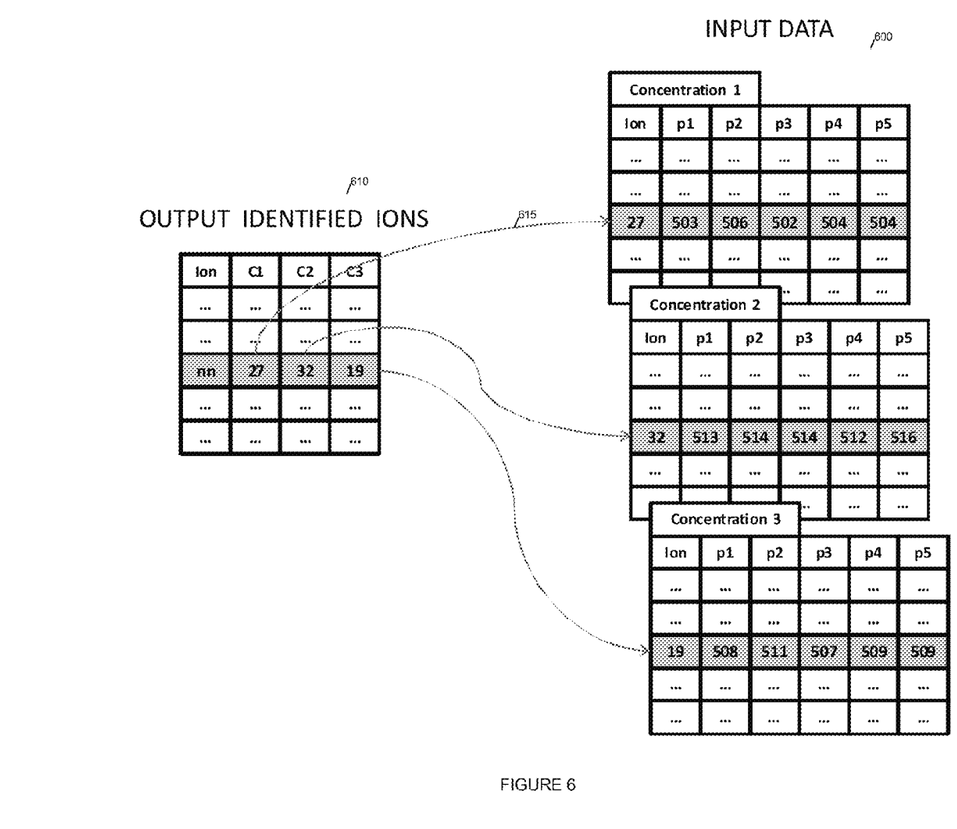
FIG. 6 shows the data structure of inputs to stage 2 of the general flowchart of FIG. 4 and the data structure of stage 2 output according to an embodiment.

FIG. 6 shows the data structure of inputs to stage 2 of the general flowchart of FIG. 4 and the data structure of stage 2 output according to an embodiment. As said before, in the method described with the flowchart of FIG. 4, the stage 2 inputs used are not mass spectra but are mass spectra equivalent data derived from the output T1 ion identification tables obtained as output of stage 1. The inputs of stage 2 consist of N tables (600), each one the output of the stage 1 process applied to a different (known) concentration of the same substance. Each row in the input tables can be associated to a "virtual" peak with an estimated mass, intensity and errors. These inputs can be processed in stage 2 by the ion identification method as the equivalent inputs data (500) which are the input mass spectra of FIG. 1. tables.

The output may consist of a table (610) with N columns—one for each concentration of the substance—and as many rows as there were identified ions at the end of stage 2. Each row contains pointers: the pointer (615) found in the column associated to a given concentration refers to a row in the input table for that concentration. Therefore, the output table produced at the end of stage 2 allows one to say that those "virtual" peaks are all associated to the same physical ion.

The invention claimed is:

1. A method performed on a computer system including a mass spectrometer and an ion identification engine to identify peaks generated by different physical ions in a solution including a certain concentration of at least one substance, the method comprising:
analyzing a solution including a concentration of a given chemical substance using the mass spectrometer to provide a plurality of mass spectrum data files; and
employing the ion identification engine for:
reading coordinates of a peak from a first mass spectrum data file in the plurality of mass spectra data files;
selecting from each mass spectrum data file other than the first mass spectrum data file, peak coordinates which are close to the read peak coordinates from the first mass spectrum, by computing a distance function qualifying a proximity between two peaks;
determining a highest scored sequence of peaks comprising the read peak from the first mass spectrum and one selected peak from each other mass spectrum by computing a scoring function qualifying a likelihood that all peaks in the sequence have been generated by a same type of physical ion;
storing the highest scored sequence only if a ratio of the highest scored sequence to a second highest scored sequence is above a limit ratio;
reading coordinates of one other peak from the first mass spectrum data file and executing the preceding selecting, determining and storing steps until all the peaks from the mass spectrum are read, each of the resulting stored sequences containing peaks, one for each mass spectrum; and
identifying different physical ions in the solution based on the stored sequences, each of the scored sequences containing peaks generated by the same physical ion.

2. The method of claim 1 further comprising:
suppressing among the stored sequences any subset of sequences which are found to include a same peak of a same mass spectrum.

3. The method of claim 1 wherein the distance function between two peaks and the scoring function depend on a mass and intensity of the two peaks.

4. The method of claim 1 wherein the distance function between two peaks depends on the mass of the peaks and the scoring function depends on a combination of the mass of the peaks and a peak concentration-intensity correlation.

5. The method of claim 1 wherein, the steps of the method of claim 1 for identifying the resulting peak sequences corresponding to ions are executed on a first set of mass spectra for a given concentration c using a first distance and a first scoring function which both depend on the mass and intensity of the peaks;
the method further comprising:
repeating the preceding steps on further sets of mass spectra, the first and further sets of mass spectra corresponding to different concentrations;
computing average mass-intensity peak coordinates for each sequence resulting from execution of the preceding steps for each solution concentration and obtaining a series of virtual peaks per each concentration; and
applying the steps of the method of claim 1 to the set of virtual mass spectra, each virtual mass spectrum corresponding to one concentration, each virtual mass spectrum comprising the computed series of virtual peaks, using a second distance function between two peaks which depends on the mass of the peaks and a second scoring function which depends on a combination of the mass of the peaks and a peak concentration-intensity correlation, the resulting sequences being the peaks corresponding to an ion in the different virtual mass spectra, each virtual mass spectrum corresponding to one solution concentration.

6. The method of claim 5 wherein the first distance d function between two mass spectra peaks $p_1$ with coordinates $x_1$ and $y_1$ and $p_2$ with coordinates $x_2$ and $y_2$ is:

$$d(p_1,p_2)=\sqrt{(x_1-x_2)^2+(y_1-y_2)^2/R^2}$$

R being a ratio between relative errors associated with the y coordinate and x coordinate.

7. The method of claim 5 wherein the first scoring of a sequence is:

$$1/\max d(p1,p2)$$

where p1, p2 are any two peaks in the sequence and d (p1, p2) is the distance between them.

8. The method of claim 5 wherein the second distance d function between two mass spectra peaks $p_1$ and $p_2$ with coordinates $x_1$ and $y_1$ and $p_2$ with coordinates $x_2$ and $y_2$ is:

$$d(p_1,p_2)=\text{absolute value}(x_1-x_2).$$

9. The method of claim 5 wherein the second scoring of a sequence is:

$$\text{correlation\_coefficient}(c1,y1,c2,y2,\ldots cN,yN)/\max d(p1,p2)$$

where p1, p2 are any two peaks in the sequence and d (p1, p2) is the distance between them.

10. The method according to claim 1, further comprising a computer program stored in a non-transitory computer readable medium.

11. A method performed on a computer system including a mass spectrometer and an ion identification engine for identifying peaks generated by different physical ions in a solution including a certain concentration of at least one substance, the method comprising:
a first process including:
analyzing a solution including a concentration of a given chemical substance using the mass spectrometer to provide a plurality of mass spectrum data files; and
employing the ion identification engine for:
reading coordinates of a peak from a first mass spectrum data file in the plurality of mass spectra data files;

selecting from each mass spectrum data file other than the first mass spectrum data file, peak coordinates which are close to the read peak coordinates from the first mass spectrum, by computing a distance function qualifying a proximity between two peaks;

determining a highest scored sequence of peaks comprising the read peak from the first mass spectrum and one selected peak from each other mass spectrum by computing a scoring function qualifying a likelihood that all peaks in the sequence have been generated by a same type of physical ion;

storing the highest scored sequence only if a ratio of the highest scored sequence to a second highest scored sequence is above a limit ratio;

reading coordinates of one other peak from the first mass spectrum data file and executing the preceding selecting, determining and storing steps until all the peaks from the mass spectrum are read, each of the resulting sequences containing peaks, one for each mass spectrum; and identifying different physical ions in the solution based on the stored sequences, each of the scored sequences containing peaks generated by the same physical ion wherein the first process is executed on a first set of mass spectra for a given concentration c using a first distance and a first scoring function which both depend on the mass and intensity of the peaks, and wherein the method further comprises:

repeating the first process on further sets of mass spectra, the first and further sets of mass spectra corresponding to different concentrations;

computing average mass-intensity peak coordinates for each sequence resulting from execution of the first process for each solution concentration and obtaining a series of virtual peaks per each concentration; and applying the steps of the of the first process to the set of virtual mass spectra, each virtual mass spectrum corresponding to one concentration, each virtual mass spectrum comprising the computed series of virtual peaks, using a second distance function between two peaks which depends on the mass of the peaks and a second scoring function which depends on a combination of the mass of the peaks and a peak concentration-intensity correlation, the resulting sequences being the peaks corresponding to an ion in the different virtual mass spectra, each virtual mass spectrum corresponding to one solution concentration.

12. The method of claim 11 wherein the first distance d function between two mass spectra peaks $p_1$ with coordinates $x_1$ and $y_1$ and $p_2$ with coordinates $x_2$ and $y_2$ is:

$$d(p_1,p_2)=\sqrt{(x_1-x_2)^2+(y_1-y_2)^2/R^2}$$

R being a ratio between relative errors associated with the y coordinate and x coordinate.

13. The method of claim 11 wherein the first scoring of a sequence is: $1/\max d(p1, p2)$ where p1, p2 are any two peaks in the sequence and d (p1, p2) is the distance between them.

14. The method of claim 11 wherein the second distance d function between two mass spectra peaks $p_1$ and $p_2$ with coordinates $x_1$ and $y_1$ and $p_2$ with coordinates $x_2$ and $y_2$ is: $d(p_1,p_2)=$absolute value$(x_1-x_2)$.

15. The method of claim 11 wherein the second scoring of a sequence is:

$$\text{correlation\_coefficient}(c1,y1,c2,y2,\ldots cN,yN)/\max d(p1,p2)$$

where p1, p2 are any two peaks in the sequence and d (p1, p2) is the distance between them.

* * * * *